United States Patent
Olbert et al.

(10) Patent No.: US 9,522,374 B2
(45) Date of Patent: Dec. 20, 2016

(54) SHELL-AND-TUBE REACTOR FOR PREPARING MALEIC ANHYDRIDE

(75) Inventors: Gerhard Olbert, Dossenheim (DE); Hans-Jürgen Bassler, Neustadt (DE); Michael Steiniger, Neustadt (DE)

(73) Assignee: BASF SE, Ludwigshafen (DE)

( * ) Notice: Subject to any disclaimer, the term of this patent is extended or adjusted under 35 U.S.C. 154(b) by 740 days.

(21) Appl. No.: 12/942,715

(22) Filed: Nov. 9, 2010

(65) Prior Publication Data
US 2011/0110830 A1 May 12, 2011

(30) Foreign Application Priority Data
Nov. 10, 2009 (EP) .................................. 09175466

(51) Int. Cl.
*B01J 8/00* (2006.01)
*B01J 8/02* (2006.01)
*B01J 8/06* (2006.01)
*B01J 19/00* (2006.01)
*B01J 19/02* (2006.01)
*C07C 51/215* (2006.01)
*C07C 51/00* (2006.01)
*C07C 51/16* (2006.01)
*C07C 51/21* (2006.01)

(52) U.S. Cl.
CPC .............. *B01J 8/067* (2013.01); *B01J 19/02* (2013.01); *C07C 51/215* (2013.01); *B01J 2219/00245* (2013.01); *B01J 2219/0286* (2013.01)

(58) Field of Classification Search
CPC .............. B01J 8/00; B01J 8/02; B01J 8/06; B01J 8/067; B01J 19/00; B01J 19/02; B01J 2219/00049; B01J 2219/00245; B01J 2219/02; B01J 2219/025; B01J 2219/0277; B01J 2219/0386; C07C 51/00; C07C 51/16–51/215
USPC ....... 422/129, 187, 198, 211, 600, 650, 651, 422/659
See application file for complete search history.

(56) References Cited

U.S. PATENT DOCUMENTS

| | | | |
|---|---|---|---|
| 4,933,312 A | 6/1990 | Haddad et al. | |
| 5,095,125 A | 3/1992 | Haddad et al. | |
| 5,137,860 A | 8/1992 | Ebner et al. | |
| 5,275,996 A | 1/1994 | Andrews et al. | |
| 5,641,722 A | 6/1997 | Mitchell et al. | |
| 6,803,473 B2 * | 10/2004 | Weiguny et al. | 549/259 |
| 7,509,928 B2 * | 3/2009 | Becker et al. | 122/450 |
| 8,721,997 B2 | 5/2014 | Hechler et al. | |
| 9,126,171 B2 | 9/2015 | Schliephake et al. | |
| 2003/0065194 A1 | 4/2003 | Weiguny et al. | |
| 2006/0004226 A1 | 1/2006 | Machhammer et al. | |
| 2008/0023175 A1 | 1/2008 | Lehr et al. | |
| 2008/0260605 A1 * | 10/2008 | Dieterle et al. | 422/188 |
| 2010/0024614 A1 * | 2/2010 | Rex et al. | 83/13 |
| 2011/0110830 A1 | 5/2011 | Olbert et al. | |

FOREIGN PATENT DOCUMENTS

| | | |
|---|---|---|
| DE | 10011309 A1 | 9/2001 |
| DE | 10 2007 025869 A1 | 7/2008 |
| DE | 10 2007 035046 A1 | 1/2009 |
| EP | 0056901 A2 | 8/1982 |
| EP | 1882518 A2 | 1/2008 |
| RU | 2012 123 724 A | 12/2013 |
| SU | 980619 A3 | 12/1982 |
| WO | WO-2008/000740 A1 | 1/2008 |

OTHER PUBLICATIONS

Euro Steel, Stainless Steel—Approximate Internation Equivalents of some of the more common types of stainless steel, 2006.*
Ullman's Encyclopedia of Industrial Chemistry, 6th Edition, 1999 Electronic Release, Chapter "Maleic and Fumaric Acid—Maleic Anhydrid," 11 pages total.

* cited by examiner

*Primary Examiner* — Natasha Young
(74) *Attorney, Agent, or Firm* — Drinker Biddle & Reath LLP

(57) ABSTRACT

Apparatus for preparing maleic anhydride by heterogeneously catalyzed gas-phase oxidation of a stream containing hydrocarbons having at least 4 carbon atoms per molecule, which includes a reactor with reaction tubes into which a solid-state catalyst over which the exothermic reaction of the stream with an oxygen-comprising gas stream takes place is introduced and one or more pumps and heat exchangers located outside the reactor and through which a heat transfer medium formed by a salt melt flows through the intermediate space in the reactor between the reaction tubes and takes up the heat of reaction, with the temperature of the melt being in the range from 350 to 480° C. The reaction tubes are made of a heat-resistant alloy steel which includes at least 0.5% by weight of chromium or at least 0.25% by weight of molybdenum or both.

11 Claims, No Drawings

SHELL-AND-TUBE REACTOR FOR PREPARING MALEIC ANHYDRIDE

CROSS REFERENCE TO RELATED APPLICATIONS

This application is a non-provisional application which, claims benefit to European application 09175466.3, filed Nov. 10, 2009, the entire disclosures of which is hereby incorporated by reference.

The invention relates to an apparatus comprising a shell-and-tube reactor for preparing maleic anhydride (hereinafter referred to as MAn for short) by heterogeneously catalyzed gas-phase oxidation of hydrocarbons having at least four carbon atoms by means of oxygen-comprising gases in the presence of a volatile phosphorus compound over a catalyst comprising vanadium, phosphorus and oxygen.

MAn is mainly used in the production of unsaturated polyester resins which are used as composites in the construction and automobile industry. In addition, MAn is an important intermediate in the synthesis of gamma-butyrolactone, tetrahydrofuran and 1,4-butanediol, which are in turn used as solvents or, for example, are processed further to form polymers such as polytetrahydrofuran or polyvinylpyrrolidone.

The preparation of MAn by heterogeneously catalyzed gas-phase oxidation of hydrocarbons having at least four carbon atoms by means of oxygen in a shell-and-tube reactor over a solid-state catalyst is generally known and is described, for example, in Ullmann's Encyclopedia of Industrial Chemistry, 6th Edition, 1999 Electronic Release, Chapter "MALEIC AND FUMARIC ACID—Maleic Anhydride". In general, benzene or $C_4$-hydrocarbons such as 1,3-butadiene, n-butenes or n-butane are used for this purpose.

Preference is given to using solid-state catalysts comprising vanadium, phosphorus and oxygen as active composition.

The catalysts comprising vanadium, phosphorus and oxygen, which are hereinafter referred to as "VPO catalysts", are used in unpromoted or promoted form.

The conversion of the hydrocarbons into MAn over such VPO catalysts proceeds strongly exothermically.

These gas-phase reactions are usually carried out at reaction temperatures in the range from 390° C. to 500° C.

Reactors in which these strongly exothermic heterogeneously catalyzed gas-phase reactions can be carried out on an industrial scale are described, for example, in EP 1 882 518 A2.

These are shell-and-tube reactors in which the reaction tubes filled with the VPO catalyst are arranged vertically and a heat transfer medium flows around the outsides of the reaction tubes.

To control the temperature of the strongly exothermic gas-phase reaction in the reaction tubes, use is made of heat transfer media comprising, for example, liquid salt melts. Mixtures of alkali metal nitrates and alkali metal nitrites, for example potassium nitrate, sodium nitrite and sodium nitrate, having a preferably eutectic composition have been found to be particularly useful.

Although the use of such salt melts at temperatures up to 620° C. would be conceivable, the temperature of the salt melt is limited to about 450° C.-480° C. This takes account of both the thermal stability of the salt mixture and also the requirements in terms of reaction conditions for a gas-phase oxidation of hydrocarbons to produce MAn.

Owing to the temperature ranges for the salt melt on a continuous basis of from 350 to 480° C. necessary in the MAn production processes, the materials used for the construction of the shell-and-tube reactor and its necessary peripheral apparatuses such as heat exchangers and pumps have to meet particular requirements.

The reaction tubes of shell-and-tube reactors used for preparing MAn have hitherto been made of heat-resistant unalloyed steels, i.e. steels comprising only iron and carbon and in addition the usual accompanying elements from the steel production process, in particular phosphorus, sulfur and silicon, but no deliberately added alloying elements. The heat-resistant unalloyed steels St 35.8 or St 37.8 which are approved for operating temperatures of up to 480° C. in accordance with EN 10216-2 or EN 10217-2 are frequently used as materials for the reaction tubes of shell-and-tube reactors for preparing MAn. These materials should therefore be able to be used without problems at the temperatures of from about 350 to 480° C., preferably from about 380 to 440° C., particularly preferably from about 390 to 430° C., customary for the salt melt in MAn reactors without a deterioration in their mechanical properties.

However, in the operation of MAn reactors whose reaction tubes have been produced from the above heat-resistant unalloyed steels, temperature- and time-dependent damage which leads to a significant deterioration in the strength values, in particular the creep strength, and cannot be attributed to creep damage has been observed.

In the light of the above, it was an object of the invention to provide an apparatus for preparing MAn which comprises a shell-and-tube reactor, does not have the above disadvantages and displays, in particular, increased creep strengths.

The object is achieved by an apparatus for preparing MAn by gas-phase oxidation of a feed stream comprising hydrocarbons having at least 4 carbon atoms per molecule, which comprises a reactor having a bundle of reaction tubes into which a solid-state catalyst over which the exothermic reaction of the feed stream with an oxygen-comprising gas stream takes place has been introduced and also one or more pumps and one or more heat exchangers which are located outside the reactor and through which a heat transfer medium formed by a salt melt flows through the intermediate space in the reactor between the reaction tubes and takes up the heat of reaction, with the temperature of the salt melt being in the range from 350 to 480° C., wherein the reaction tubes are made of a heat-resistant alloy steel which comprises either at least 0.5% by weight of chromium or at least 0.25% by weight of molybdenum or at least 0.5% by weight of chromium and at least 0.25% by weight of molybdenum.

For the abovementioned temperature range from 350 to 480° C., it has been found that the addition of the alloying element chromium in a proportion of at least 0.5% by weight, i.e. in a proportion of 0.5% by weight or higher, and/or addition of the alloying element molybdenum in a proportion of at least 0.25% by weight, i.e. in a proportion of 0.25% by weight or higher, enables the significant, time- and temperature-dependent deterioration observed in the mechanical properties, in particular the creep strength to be avoided.

If the reaction tubes are made of a heat-resistant alloy steel comprising at least 0.5% by weight of chromium and/or at least 0.25% by weight of molybdenum, a generally sufficient creep strength of the apparatus, in particular, can be ensured as long as the other components of the apparatus which come into contact with the heat transfer medium formed by a salt melt which preferably comprises alkali metal nitrates and alkali metal nitrites, in particular the tube plates in which the catalyst tubes are fastened, in particular welded, and the one or more heat exchangers located outside the reactor are made of a heat-resistant steel comprising at least 0.25% by weight of molybdenum. A suitable material for this purpose is, for example, the material 16 Mo3.

In a preferred embodiment, all other components of the apparatus in addition to the reaction tubes which come into contact with the heat transfer medium formed by a salt melt are also made of a heat-resistant alloy steel comprising either at least 0.5% by weight of chromium or at least 0.25% by weight of molybdenum or at least 0.5% by weight of chromium and at least 0.25% by weight of molybdenum.

The temperature of the salt melt which flows through the intermediate space in the reactor between the reaction tubes and takes up the heat of reaction is in the range from 350 to 480° C., preferably in the range from 380 to 440° C., particularly preferably in the range from 390 to 430° C.

The solid-state catalyst which is introduced into the reaction tubes and over which the heterogeneously catalyzed gas-phase oxidation of the feed stream comprising hydrocarbons having at least 4 carbon atoms per molecule by reaction with an oxygen-comprising gas stream takes place preferably comprises vanadium, phosphorus and oxygen as active composition (known as VPO catalyst). If a VPO catalyst is used, the feed stream generally comprises a volatile phosphorus compound.

As salt melt which is passed as heat transfer medium through the intermediate space in the reactor between the reaction tubes, preference is given to using a salt melt comprising alkali metal nitrates and alkali metal nitrites. Particular preference is given to using a salt melt having a eutectic composition, i.e., for example, comprising 53% by weight of potassium nitrate, 40% by weight of sodium nitrite and in addition 7% by weight of sodium nitrate.

Pressure-pulse-resistant reactors without bursting disks can, in particular, also be used in the apparatus of the invention.

Although the damage mechanism is not known in detail, it has been found that use of a heat-resistant alloy steel which must comprise either at least 0.5% by weight of chromium or at least 0.25% by weight of molybdenum or at least 0.5% by weight of chromium and at least 0.25% by weight of molybdenum enables the significant deterioration observed in the mechanical properties of the reaction tubes, which leads to the shell-and-tube reactors used for MAn production having to be replaced prematurely, to be avoided.

The invention is not restricted in terms of the concrete configuration of the apparatus for preparing MAn:

It can be applied to all MAn plants in which MAn is prepared in a shell-and-tube reactor having a bundle of reaction tubes, where a solid-state catalyst, preferably a VPO catalyst, is introduced into the reaction tubes and a feed stream comprising hydrocarbons having at least 4 carbon atoms per molecule and preferably a volatile phosphorus compound and a gas stream comprising molecular oxygen are passed over the catalyst in cocurrent or in countercurrent relative to the flow direction of the salt melt.

A heat transfer medium formed by a salt melt is passed through the space within the shell, i.e. the intermediate space between the reaction tubes, to remove the heat of reaction of the strongly exothermic reaction. Mixtures of alkali metal nitrates and alkali metal nitrites have been found to be particularly useful here.

The salt melt is conveyed by means of one or more pumps through the space within the shell of the shell-and-tube reactor and through one or more external heat exchangers, in particular salt bath coolers, steam superheaters and electric heaters.

In the apparatus of the invention, preference is given to all components of the apparatus which come into contact with the salt melt, in particular the reaction tubes, the reactor shell, the tube plates into which the reaction tubes are welded and also the one or more pumps which convey the salt melt and the one or more heat exchangers which are located outside the reactor and through which the salt melt is passed, in particular salt bath coolers, steam superheaters and electric heaters, being made of a material which comprises either at least 0.5% by weight of chromium or at least 0.25% by weight of molybdenum or at least 0.5% by weight of chromium and at least 0.25% by weight of molybdenum.

Preference is given to using a heat-resistant alloy steel which comprises one or more of the further alloying elements titanium, niobium and vanadium in addition to either at least 0.5% by weight of chromium or at least 0.25% by weight of molybdenum or at least 0.5% by weight of chromium and at least 0.25% by weight of molybdenum.

These are, for example, preferably materials which correspond to the standard EN 10217-2 for welded tubes made of heat-resistant steels or EN 10216-2 for seamless tubes made of heat-resistant steels and are denoted by the material abbreviations 16Mo3, 13CrMo4-5, 10CrMo9-10 or X6CrNiTi18-10 and have the corresponding EN material numbers 1.5415, 1.7335, 1.7380 and 1.4541, respectively.

The apparatus can preferably comprise a reactor whose space-time yield is optimized by means of a multizone configuration, i.e. a reactor having two or more successive reaction zones having differing activities of the catalyst and/or differing temperatures of the heat transfer medium formed by the salt melt.

Such an apparatus is known, for example from DE-A 100 11 309: it comprises a shell-and-tube reactor unit having at least two successive cooled reaction zones, where the temperature of the first reaction zone is from 350 to 450° C. and the temperature of the second reaction zone and any further reaction zones is from 350 to 480° C. and the temperature difference between the hottest reaction zone and the coldest reaction zone is at least 2° C.

Here, the term shell-and-tube reactor unit refers to a unit comprising at least one shell-and-tube reactor.

The term reaction zone refers to a region which is located within a shell-and-tube reactor and comprises catalyst and within which the temperature is maintained at a uniform value. If this temperature is not exactly the same at all places, the term refers to the number average of the temperatures along the reaction zone. The first, second or further reaction zone is in each case the first, second or further reaction zone in the direction in which the gas flows.

Suitable hydrocarbons are, as is customary in MAn processes, aliphatic and aromatic, saturated and unsaturated hydrocarbons having at least four carbon atoms, for example 1,3-butadiene, 1-butene, 2-cis-butene, 2-trans-butene, n-butane, $C_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, C5 mixture, hexenes, hexanes, cyclohexane and benzene. Preference is given to using 1-butene, 2-cis-butene, 2-trans-butene, n-butane, benzene or mixtures thereof. Particular preference is given to using n-butane, for example as pure n-butane or as component in n-butane-comprising gases and liquids. The n-butane used can originate, for example, from natural gas, from steam crackers or FCC plants.

Oxidants used are gases comprising molecular oxygen, for example air, synthetic air, a gas enriched with oxygen or "pure" oxygen, i.e., for example, oxygen from the fractionation of air.

To ensure a long catalyst operating life and a further increase in conversion, selectivity, yield, space velocity over the catalyst and space-time yield, a volatile phosphorus compound is usually introduced in an amount-regulated manner into the reaction gas. Preference is given to using tri($C_1$-$C_4$-alkyl) phosphates. The required amount of the phosphorus compound is dependent on various parameters, for example the type and amount of catalyst or, for example, the temperatures in the apparatus, and has to be adapted for each system. Preference is given to a content of from 0.2 to 20 ppm by volume, particularly preferably from 0.5 to 5 ppm by volume.

Preferred catalysts for the process of the invention are all those whose active composition comprises vanadium, phosphorus and oxygen. Thus, it is possible to use, for example, catalysts which do not comprise any promoters, as described, for example, in U.S. Pat. No. 5,275,996, U.S. Pat. No. 5,641,722, U.S. Pat. No. 5,137,860, U.S. Pat. No. 5,095,125, U.S. Pat. No. 4,933,312 or EP-A-0 056 901.

As regards the use of the catalyst in the process of the invention, various variants are possible. In the simplest case, all reaction zones of the shell-and-tube reactor unit are charged with the same catalyst bed. For the present purposes, a catalyst bed is catalyst material which has, on average, the same composition and the same activity per unit volume. A catalyst bed can be composed of shaped bodies of the same catalyst, of shaped bodies of a mixture of different catalysts or of shaped bodies (same catalyst or mixture of different catalysts) which have been mixed with an inert material, i.e. "diluted". In a second variant, different catalyst beds are used in different reaction zones. The use of a less active catalyst bed in the first reaction zone or one or more of the front reaction zones and the use of more active catalyst bed in one or more of the later reaction zones may thus be advantageous. Furthermore, it is also possible to use various catalyst beds within one and the same reaction zone. In this variant, too, it may be advantageous to use a less active catalyst bed in the vicinity of the reactor inlet and to use a more active catalyst bed downstream thereof.

The individual reaction zones can be realized in one shell-and-tube reactor as multizone shell-and-tube reactor or in a plurality of shell-and-tube reactors which are connected in series and can in turn comprise one or more reaction zones. For the purposes of the present invention, a multizone shell-and-tube reactor is a shell-and-tube reactor which comprises at least two circuits for heat transfer media and makes it possible for different temperatures to be set in a targeted manner in the individual reaction zones.

The invention is illustrated below with the aid of examples.

EXAMPLES

| Example* | Hours of operation | Operating temp. (salt bath) [° C.] | Material of reaction tube | Minimum values of the mechanical properties in accordance with DIN | Microstructure finding |
|---|---|---|---|---|---|
| A (for comparison) | ca. 76 000 | 400-435 | St 37.8 | not fulfilled | damage |
| B (according to the invention) | ca. 50 000 | 400-435 | 16Mo3 | fulfilled | damage-free |
| C (for comparison) | ca. 47 000 | 400-435 | St 37.8 | not fulfilled | damage |
| D (according to the invention) | ca. 68 000 | 400-435 | 1.4541 | fulfilled | damage-free |

Description of the Examples

In routine tests on tubes made of the material St 37.8 from an MAn reactor which has been operated for about 76,000 h, it was found that the mechanical properties, determined in a tensile test, were below the minimum values required in the standard. Microstructural examinations show that the cause of this decrease in strength was a temperature-induced microstructural change in the material which is not attributable to creep damage. Tubes were then withdrawn at various places in the reactor and examined in the same way. The above-described change in the material could be detected in all tubes examined.

Owing to this finding, the examinations of tubes were extended to other reactors which are operated in the same temperature region but have been operated for different times. Likewise, pilot reactors provided with tubes made of other materials were checked in the temperature region indicated. It was found, firstly, that the materials effect described is not only temperature-dependent but also time-dependent and damage to the material St 37.8 which progresses with time can be deduced therefrom. Secondly, it was found that the above-described disadvantageous change in the material occurs only in the case of unalloyed steels in the temperature range indicated but not in the case of steels which comprise at least 0.5% by weight of Cr and/or at least 0.25% by weight of Mo. Based on the results of the examinations, unalloyed steels are not suitable for use in Man reactors at the operating temperatures of >400° C. which usually prevail therein. In contrast, steel alloys comprising at least 0.5% of Cr and/or at least 0.25% of Mo are suitable.

The invention claimed is:

1. An apparatus for preparing maleic anhydride by heterogeneously catalyzed gas-phase oxidation of a feed stream comprising hydrocarbons having at least 4 carbon atoms per molecule, which comprises a reactor having a bundle of reaction tubes into which a solid-state catalyst over which the exothermic reaction of the feed stream with an oxygen-comprising gas stream takes place has been introduced and also one or more pumps and one or more heat exchangers which are located outside the reactor and through which a heat transfer medium formed by a salt melt flows through the intermediate space in the reactor between the reaction tubes and takes up the heat of reaction, with the temperature of the salt melt being in the range from 350 to 480° C., wherein the reaction tubes are made of one of the following heat-resistant alloy steels: material abbreviation 16Mo3, corresponding to the EN material number 1.5415, material abbreviation 13 CrMo4-5, corresponding to the EN material number 1.7335 or material abbreviation 10CrMo9-10 corresponding to the EN material number 1.7380, and wherein in addition to the reaction tubes, all other components of the apparatus which come into contact with the salt melt as heat transfer medium are made of one of the following heat-resistant alloy steels: material abbreviation 16Mo3, corresponding to the EN material number 1.5415, material abbreviation 13 CrMo4-5, corresponding to the EN material number 1.7335 or material abbreviation 10CrMo9-10 corresponding to the EN material number 1.7380.

2. The apparatus according to claim 1, wherein the feed stream comprises a volatile phosphorus compound and the solid-state catalyst comprises vanadium, phosphorus and oxygen.

3. The apparatus according to claim 2, wherein tri($C_1$-$C_4$-alkyl) phosphate is used as volatile phosphorus compound.

4. The apparatus according to claim 1, wherein the temperature of the salt melt is in the range from 380.degree. C. to 440.degree. C.

5. The apparatus according to claim 1, wherein the salt melt comprises alkali metal nitrates and alkali metal nitrites.

6. The apparatus according to claim 1, wherein the salt melt has the eutectic composition of a mixture of potassium nitrate, sodium nitrite and sodium nitrate.

7. The apparatus according to claim 6, wherein the salt melt comprises 53% by weight of potassium nitrate, 40% by weight of sodium nitrite and 7% by weight of sodium nitrate.

8. The apparatus according to claim 1, wherein n-butane is used as the hydrocarbon.

9. The apparatus according to claim 1, wherein the heat-resistant alloy steel additionally comprises one or more of the alloying elements titanium, niobium and vanadium.

10. The apparatus according to claim 1, wherein the shell-and-tube reactor has two or more successive reaction zones having differing activities of the solid-state catalyst and/or differing temperatures of the heat transfer medium formed by a salt melt.

11. The apparatus according to claim 1, wherein the shell-and-tube reactor has two or more successive reaction zones having differing activities of the solid-state catalyst and/or differing temperatures of the heat transfer medium formed by a salt melt; wherein the salt melt comprises 53% by weight of potassium nitrate, 40% by weight of sodium nitrite and 7% by weight of sodium nitrate; and wherein n-butane is used as the hydrocarbon.

\* \* \* \* \*